United States Patent
Guevremont

(10) Patent No.: US 7,358,504 B2
(45) Date of Patent: Apr. 15, 2008

(54) FAIMS APPARATUS AND METHOD FOR SEPARATING IONS

(75) Inventor: Roger Guevremont, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 375 days.

(21) Appl. No.: 10/529,306

(22) PCT Filed: Jul. 10, 2003

(86) PCT No.: PCT/CA03/01051

§ 371 (c)(1),
(2), (4) Date: Mar. 25, 2005

(87) PCT Pub. No.: WO2004/029614

PCT Pub. Date: Apr. 8, 2004

(65) Prior Publication Data

US 2006/0097156 A1     May 11, 2006

Related U.S. Application Data

(60) Provisional application No. 60/413,162, filed on Sep. 25, 2002.

(51) Int. Cl.
*H01J 49/42* (2006.01)
(52) U.S. Cl. ................................. 250/396 R
(58) Field of Classification Search ............ 250/396 R, 250/281, 282, 287, 286, 292, 288
See application file for complete search history.

(56) References Cited

U.S. PATENT DOCUMENTS 5,420,424 A     5/1995   Carnahan et al.

(Continued)

FOREIGN PATENT DOCUMENTS

WO    WO 01/22049    3/2001

OTHER PUBLICATIONS

Guevremont, et al. "Atmospheric pressure ion trapping in a tandem FAIMS-FAIMS coupled to a TOFMS: studies with electrospray generated gramicidin S ions." J. Am. Soc. Mass Spectrom. 2001, 12, 1320-1330.*

(Continued)

*Primary Examiner*—Robert Kim
*Assistant Examiner*—Michael Maskell
(74) *Attorney, Agent, or Firm*—Freedman & Associates

(57) ABSTRACT

Disclosed is a high field asymmetric waveform ion mobility spectrometer (FAIMS) for separating ions, and a method therefore. The FAIMS includes an electrode stack (24) having a length and comprising a plurality of electrodes (26, 28). Each electrode of the electrode stack is spaced apart from an adjacent electrode in a direction along the length of the electrode stack, and each electrode of the electrode stack has an edge that defines a portion of an edge of the electrode stack. At least an electrode (22) is spaced apart from the edge of the electrode stack in a direction approximately transverse to the length of the electrode stack, the space between the at least an electrode and the edge of the electrode stack defines an analytical gap (20) for allowing ions to propagate therebetween. Ions are separated as they move through an electric field within the analytical gap resulting from the application of an asymmetric waveform voltage to alternate electrodes of the electrode stack and application of a direct current voltage to at least some of the electrodes of the electrode stack and to the at least an electrode.

25 Claims, 11 Drawing Sheets

U.S. PATENT DOCUMENTS

| | | | |
|---|---|---|---|
| 5,789,745 A | 8/1998 | Martin et al. | |
| 6,495,823 B1 | 12/2002 | Miller et al. | |
| 6,504,149 B2 | 1/2003 | Guevremont et al. | |
| 6,512,224 B1 | 1/2003 | Miller et al. | |
| 6,621,077 B1 | 9/2003 | Guevremont et al. | |
| 6,639,213 B2 * | 10/2003 | Gillig et al. | 250/286 |
| 6,653,627 B2 * | 11/2003 | Guevremont et al. | 250/288 |
| 6,690,004 B2 | 2/2004 | Miller et al. | |
| 6,703,609 B2 | 3/2004 | Guevremont et al. | |
| 6,727,496 B2 | 4/2004 | Miller et al. | |
| 6,744,043 B2 * | 6/2004 | Loboda | 250/287 |
| 6,753,522 B2 * | 6/2004 | Guevremont et al. | 250/287 |
| 6,770,875 B1 | 8/2004 | Guevremont et al. | |
| 6,806,466 B2 | 10/2004 | Guevremont et al. | |
| 6,825,461 B2 | 11/2004 | Guevremont et al. | |
| 2001/0030285 A1 * | 10/2001 | Miller et al. | 250/288 |
| 2001/0032929 A1 * | 10/2001 | Fuhrer et al. | 250/281 |
| 2003/0047681 A1 * | 3/2003 | Guevremont et al. | 250/288 |
| 2003/0150984 A1 * | 8/2003 | Guevremont et al. | 250/281 |
| 2003/0150985 A1 * | 8/2003 | Guevremont et al. | 250/287 |
| 2006/0049363 A1 | 3/2006 | Geuvremont | |
| 2006/0151694 A1 | 7/2006 | Guevremont et al. | |

OTHER PUBLICATIONS

Guevremont, et al. "Electrospray ionization high-field asymmetric waveform mobility spectrometrey—mass spectrometry." Analytical Chemistry, vol. 71, No. 13, Jul. 1, 1999.*

* cited by examiner

FAIMS APPARATUS AND METHOD FOR SEPARATING IONS

This application claims the benefit of U.S. Provisional Application No. 60/413,162 filed on Sep. 25, 2002.

FIELD OF THE INVENTION

The instant invention relates generally to high field asymmetric waveform ion mobility spectrometry (FAIMS), more particularly the instant invention relates to a FAIMS apparatus having stacked electrodes and a method therefore.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength. In this application, electric field E will be used for simplicity to denote the more accurate term E/N where N is the number density of the bath gas.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $V_L = KE_L$, where K is the low field ion mobility under operating pressure and temperature conditions. The distance traveled is $d_L = V_L t_L = KE_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Several versions of parallel plate FAIMS and multiple plate FAIMS are known in the art. In each case, ions are introduced into the FAIMS system via an ion inlet, and are carried between the plates by a flow of a gas. The ions are transported from an inlet edge of the plates to an opposite outlet edge of the plates by the flow of a gas, during which time the ions are separated. For instance, those ions having appropriate high field mobility properties for a given combination of applied DV and CV are selectively transmitted between the plates. Of course, some of these ions are lost through collisions with the plates, since the ions are free to diffuse in any of 3 dimensions, including in a direction towards the plates.

It is a limitation of the prior art flat plate FAIMS that the cross section of the beam of transmitted ions is large compared to the size of the ion outlet. This results in poor transmission to a detector or to another analyzer arranged in tandem with the FAIMS. It is therefore an object of the instant invention to provide an apparatus that improves ion extraction for a flat plat FAIMS analyzer.

SUMMARY OF THE INVENTION

In accordance with an aspect of the instant invention there is provided an apparatus for separating ions comprising an electrode stack having a length and comprising a plurality of electrodes, each electrode of the electrode stack being spaced apart from an adjacent electrode of the electrode stack in a direction along the length of the electrode stack, each electrode of the electrode stack having an edge defining a portion of an edge of the electrode stack; at least an electrode spaced apart from the edge of the electrode stack in a direction transverse to the length of the electrode stack, the space between the at least an electrode and the edge of the electrode stack defining an analytical gap for allowing ions to propagate therebetween; and, at least an electrical controller for electrically coupling to at least one of an electrode of the plurality of electrodes of the electrode stack and the at least an electrode, for applying an asymmetric waveform voltage between the electrode of the plurality of electrodes of the electrode stack and the at least an electrode and for applying a direct current voltage between the electrode of the plurality of electrodes of the electrode stack and the at least an electrode so as to establish an electric field within the analytical gap.

In accordance with another aspect of the instant invention there is provided an apparatus for separating ions comprising: a first electrode stack having a length and comprising a plurality of electrode plates, each electrode plate of the first electrode stack being spaced apart from an adjacent electrode plate in a direction along the length of the first electrode stack, each electrode plate of the first electrode stack having an edge defining a portion of an edge of the first electrode stack; a second electrode stack having a length, the length of the second electrode stack being substantially similar to the length of the first electrode stack, the second electrode stack comprising a second plurality of electrode plates, each electrode plate of the second electrode stack being spaced apart from an adjacent electrode plate in a direction along the length of the second electrode stack, each electrode plate of the second electrode stack having an edge defining an edge of the second electrode stack, the edge of the second electrode stack facing the edge of the first electrode stack in a spaced apart arrangement and defining an analytical gap for allowing ions to propagate therebetween; and, at least an electrical controller for electrically coupling to at least one of an electrode plate of the first plurality of electrode plates of the first electrode stack and an electrode plate of the second plurality of electrode plates of the second electrode stack, for applying an asymmetric waveform voltage between the first electrode stack and the second electrode stack and for applying a direct current voltage between the first electrode stack and the second electrode stack so as to establish an electric field within the analytical gap.

In accordance with yet another aspect of the instant invention there is provided an apparatus for separating ions comprising: an electrode stack having a length and comprising a plurality of electrodes, each electrode of the electrode stack being spaced apart from an adjacent electrode in a direction along the length of the electrode stack; an electrode plate spaced apart from the electrode stack and having a surface facing the plurality of electrodes of the electrode stack and being oriented such that a minimum distance between each electrode of the electrode stack and the surface of the electrode plate is substantially a same minimum distance, as measured in a direction normal to a portion of the surface of the electrode plate proximate each electrode of the electrode stack, the space between the flat electrode plate and the electrode stack defining an analytical gap for allowing ions to propagate therethrough in a direction along the length of the electrode stack; and, at least an electrical controller for electrically coupling to at least one of an electrode of the plurality of electrodes of the electrode stack and the flat electrode plate, for applying an asymmetric waveform voltage between the electrode of the plurality of electrodes of the electrode stack and the flat electrode plate and for applying a direct current voltage between the electrode of the plurality of electrodes of the electrode stack and the flat electrode plate so as to establish an electric field within the analytical gap.

In accordance with still another aspect of the instant invention there is provided an apparatus for separating ions comprising: an electrode assembly including; at least a first electrode comprising a first plurality of electrode portions; at least a second electrode comprising a second plurality of electrode portions arranged in alternating sequence with the first plurality of electrode portions along a first direction; an electrode plate spaced apart from the first plurality of electrode portions and the second plurality of electrode portions in a second direction transverse to the first direction, the space between the electrode plate and the first plurality of electrode portions and the second plurality of electrode portions defining an analytical gap for allowing ions to propagate therethrough along approximately the first direction; and, at least an electrical controller for electrically coupling to at least one of the at least a first electrode, the at least a second electrode and the electrode plate for establishing an electrical field within the analytical gap resulting from the application of an asymmetric waveform voltage and a direct current voltage between the at least a first electrode, the at least a second electrode and the electrode plate, whereby ions having suitable high field mobility properties for a given combination of applied asymmetric waveform voltage and direct current voltage are selectively transmitted through the analytical gap.

In accordance with still another aspect of the instant invention there is provided an apparatus for separating ions comprising: at least an electrical controller; and, an electrode assembly including; at least a first electrode comprising a first plurality of electrode portions in electrical communication with the at least an electrical controller for receiving at least an asymmetric waveform voltage; at least a second electrode comprising a second plurality of electrode portions arranged in alternating sequence with the first plurality of electrode portions along a first direction, the second plurality of electrode portions in electrical communication with the at least an electrical controller for receiving a direct current voltage; at least a third electrode spaced apart from the at least a first electrode and the at least a second electrode in a second direction transverse to the first direction, the at least a third electrode comprising a third plurality of electrode portions in electrical communication with the at least an electrical controller for receiving at least an asymmetric waveform voltage; and, at least a fourth electrode comprising a fourth plurality of electrode portions arranged in alternating sequence with the third plurality of electrode portions along the first direction, the fourth plurality of electrode portions in electrical communication with the at least an electrical controller for receiving a direct current voltage, wherein the space between the at least a third electrode and the at least a first electrode defines an analytical gap for selectively transmitting ions passing therethrough along approximately the first direction at a given combination of applied asymmetric waveform and direct current voltages.

In accordance with still another aspect of the instant invention there is provided a method of separating ions comprising the steps of: introducing ions into a first space defined between adjacent electrode plates of a stacked parallel plate high field asymmetric waveform ion mobility spectrometer; performing a first separation of the ions within the first space, to selectively transmit a subset of the ions along a first direction between a first end of the electrode plates and a second end of the electrode plates that is opposite the first end; performing a second separation of the ions within a second space defined between the second end of the electrode plates and at least another electrode, to selectively transmit some of the subset of the ions along a second direction approximately transverse to the first direction between the second end of the electrode plates and an ion outlet.

In accordance with still another aspect of the instant invention there is provided a method of separating ions comprising the steps of: providing a high field asymmetric waveform ion mobility spectrometer including a plurality of spaced-apart electrodes that are stacked one relative to another in a first direction, and at least another electrode that is spaced apart from the plurality of spaced-apart electrodes in a second direction transverse to the first direction, the space between the plurality of spaced-apart electrodes and the at least another electrode defining an analytical gap; providing an electric field within the analytical gap by the application of an asymmetric waveform voltage between the plurality of spaced-apart electrodes and the at least another electrode and by the application of a direct current voltage between the plurality of spaced-apart electrodes and the at least another electrode; and, selectively transmitting ions within the analytical gap along the first direction between an ion inlet end and an ion outlet end of the analytical gap.

BRIEF DESCRIPTION OF THE DRAWINGS

Exemplary embodiments of the invention will now be described in conjunction with the following drawings, in which similar reference numbers designate similar items:

FIG. 8b is a simplified isometric view illustrating the shape of the electrodes of the stacked electrode FAIMS analyzer of FIG. 8a;

DETAILED DESCRIPTION OF THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
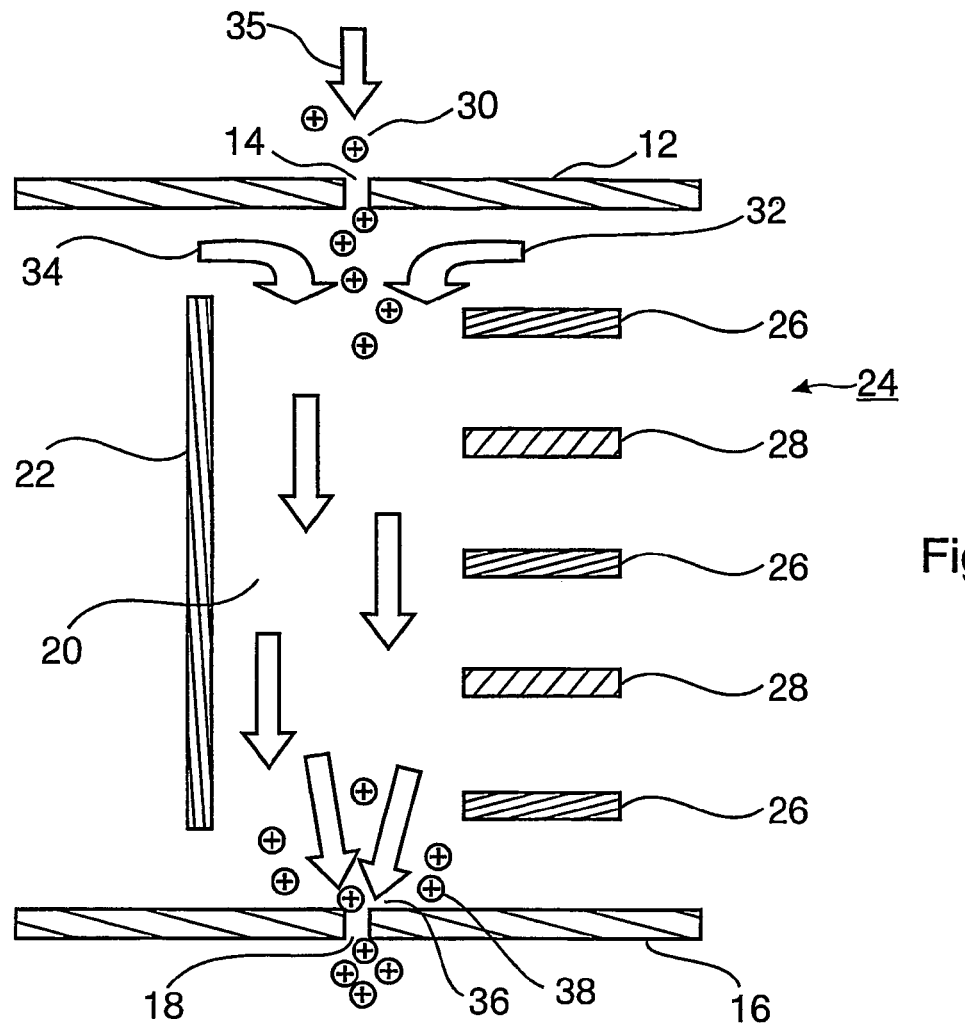
FIG. 1 is a simplified cross sectional view of a stacked parallel plate FAIMS analyzer according to an embodiment of the instant invention.

Referring to FIG. 1, shown is a simplified cross sectional view of a stacked parallel plate FAIMS analyzer according to an embodiment of the instant invention. The stacked parallel plate FAIMS analyzer, which is shown generally at 10 in FIG. 1, includes an ion inlet plate 12 with an ion inlet 14, and an ion outlet plate 16 with an ion outlet 18. A not illustrated electrically insulating material supports the plates 12 and 16 in a spaced-apart parallel arrangement. An analytical gap 20, which extends between the ion inlet plate 12 and the ion outlet plate 16, is defined between an edge of an electrode stack 24 and a facing surface of a flat plate electrode 22. The electrode stack 24 includes a plurality of electrode plates that are arranged in a spaced-apart parallel arrangement relative to one another and relative to each one of the ion inlet plate 12 and the ion outlet plate 16. Of course, the electrically insulating material in which the plurality of electrode plates and the flat plate electrode 22 are supported has been omitted in FIG. 1 for the sake of clarity.

Individual electrode plates of the electrode stack 24 are categorized into two different types of electrode plates 26 and 28, which are identified conveniently by the electric voltages applied to them by a not illustrated electrical controller. For example, each one of the electrode plates 26 has an asymmetric waveform and a dc voltage applied to it; whilst each one of the electrode plates 28 has a dc voltage applied to it, or is held at ground potential. Additionally, the flat plate electrode 22 has a dc voltage applied to it, or is held at ground potential. Optionally, different dc voltages are applied to one or both of the ion inlet plate 12 and the ion outlet plate 16. Of course, many other possible combinations of applying the dc voltages and the asymmetric waveform voltages to the electrode plates of the stacked parallel plate FAIMS analyzer 10 will be apparent to one of skill in the art. It should be understood that the above example is intended to serve only as a specific and non-limiting example to facilitate a more complete understanding of the instant invention.

Referring still to FIG. 1, ions 30 are produced at a not illustrated ionization source and enter the stacked parallel plate FAIMS analyzer 10 via ion inlet 14 in the ion inlet plate 12. Preferably, the ions are transported through the ion inlet 14 in a gas flow 35. The ions 30 pass along the analytical gap 20 between the electrode stack 24 and the flat plate electrode 22. Optionally, a gas flow 32 is provided from between one or more pairs of electrodes of the electrode stack 24, or from between an electrode of the electrode stack 24 and the ion inlet plate 12. Further optionally, a second gas flow 34 is provided from between the flat plate electrode 22 and the ion inlet plate 12. The gas flows 32, 34, and 35 converge in a region 36 adjacent to the ion outlet 18, and exit the analytical gap 20 via the ion outlet 18. Ions in the analytical gap 20 between the flat plate electrode 22 and the electrode stack 24 are channelled towards and through the ion outlet 18 as a result of the convergence of gas flows 32, 34, and 35 to the region 36 adjacent to the ion outlet 18. Since the stacked parallel plate FAIMS analyzer 10 transports and separates ions based upon the FAIMS principle, only a sub-set 38 of the original mixture of ions 30 is transported to the ion outlet 18. Some of these selectively transported ions 38 pass through the ion outlet 18, and may be transported to one of an ion detection system, another ion mobility spectrometer, or alternatively to a mass spectrometer for further analysis.

Figure 2A:
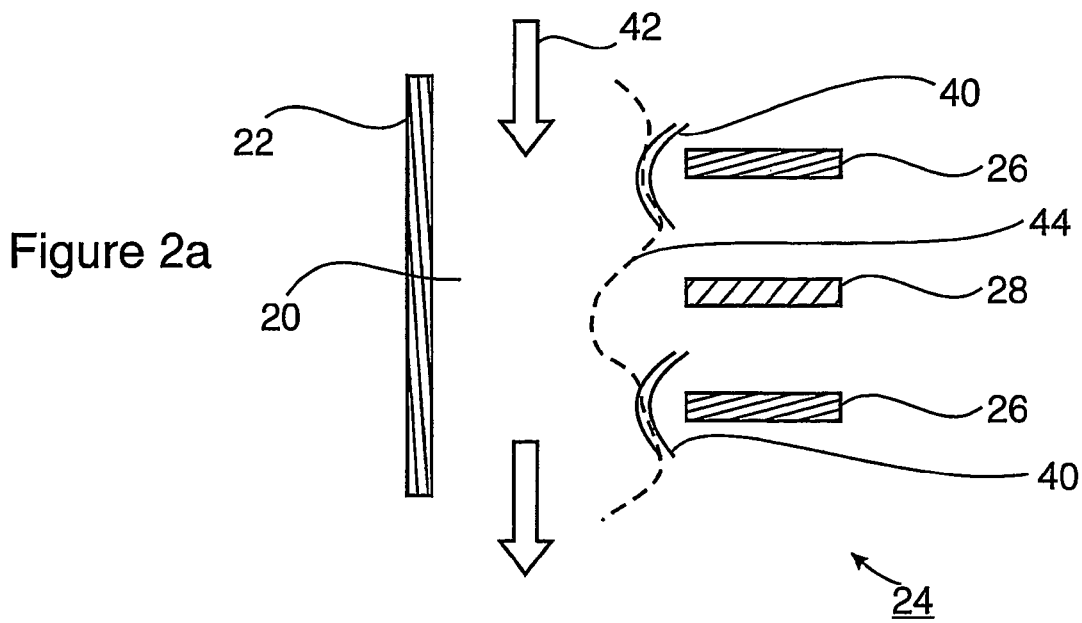
FIG. 2a illustrates the effect of electric fields within the stacked parallel plate FAIMS analyzer of FIG. 1 on the trajectory of an ion.

FIG. 2a illustrates the effect of electric fields within the stacked parallel plate FAIMS analyzer of FIG. 1 on the trajectory of an ion. Elements labeled with the same numerals have the same function as those illustrated in FIG. 1. As discussed with reference to FIG. 1, the asymmetric waveform and a dc voltage are applied to electrode plates 26, and a dc voltage (or optionally ground potential) is applied to electrode plates 28 and 22. The electric field that is established between a pair of electrode plates 26 and 28 includes a variable component relating to the application of the asymmetric waveform, and a constant in time component relating to the different dc voltages on the electrode plates, i.e. the CV. Furthermore, the application of the asymmetric waveform results in an electric field that is stronger in one polarity than in the other. Since the mobility of the ion may be higher or lower in the stronger field than in the lower field of opposite polarity, the oscillation of the ion may cause it to drift towards one of the electrodes. The dc component of the electric field is applied in order to counteract, or compensate, for this drift. Under the correct combination of asymmetric waveform and applied dc voltage difference between the electrode plates, ions with an appropriate ratio of mobility at high field to mobility at low field are in a balanced condition. In other words, the drift effect caused by the electric field arising from the applied CV just matches the drift effect caused by application of the waveform with peak voltage DV.

The electric field between electrodes 26 and 28 is constant in space, i.e. uniform between the electrodes. However, the electric field between electrodes 26 and 28 begins to change near the edges of the electrodes. The field at the edge of each electrode 26 varies in strength with distance away from the edge and extends into the analytical gap 20. The application of the DV and the CV combined with the non-uniform field at the edge results in an ion-focusing region 40 proximate to electrode 26 in which ions maintain their balanced condition. That is to say, at distances very close to the edge of electrode 26 where the field is strong the ions migrate away from the electrode 26 to the region 40, and at positions in the analytical gap 20 where the field is weaker the ions migrate towards the electrode 26 to region 40. Ions are extracted from region 40 under the influence of, for example, a gas flow 42 or a potential gradient along the length of the electrode stack.

The following is a specific and non-limiting example, and is provided in order to facilitate a better understanding of the effect of the electric fields within the stacked parallel plate FAIMS analyzer of FIG. 1 on the trajectory of an ion. In the instant example, an ion of positive polarity whose mobility increases with an increase in field strength is in a balanced condition between the electrode plates 26 and 28 with DV=+4000 volts and CV=−10 volts. In one method of application, the asymmetric waveform and the CV are both applied to electrode plates 26, and the other plates including the electrode plates 28 and the flat plate electrode 22 are held at a dc voltage of 0 V. Without consideration of the waveform, this means that the dc level of the plates 26 is −10 volts and the plates 28 and 22 are at 0 volts. Under these conditions a positively charged ion located between plates 26 and 28, or at the ends of the plates 26 adjacent to plate 22 is always attracted towards plate 26. The application of the waveform tends to counteract the motion of the ion towards plate 26, provided the mobility of the ion during the high voltage portion of the waveform is sufficiently higher than the mobility of the ion during the low voltage portion of the waveform. Ignoring the effect of the dc fields, such an ion realizes a net displacement away from electrode 26 in the time of one cycle of the waveform. When the pull of the dc fields between plates 26 and 28 is just strong enough to balance the effect caused by the asymmetric waveform, it can be assumed that if the fields originating from the waveform are increased the ions located between the plates will move away from plates 26, and if the fields of the waveform are decreased, then the ions located between the plates will tend to move towards the plates 26. The nature of the electric field changes at the edges of the plates 26 from constant to non-constant in space. Since the field is a function of distance relative to the ends of the electrodes 26, the direction and velocity of motion of the ion also becomes a function of distance. Near the end of the electrode 26 the field caused by the waveform is strong relative to the field that exists in a region between adjacent electrodes 26 and 28, and the ions move towards the balance region indicated as 40. At greater distances from the end of the electrode 26, the electric field generated from application of the waveform is weaker and the original effect of the CV, namely to attract the ions towards the plates 26, predominates.

Referring still to FIG. 2a, the ion trajectory is a result of selecting the appropriate combination of dc voltages to apply to the electrodes 26, 28 and 22. The waveform is applied (in this example) to electrodes 26. The dc voltages applied to 26, 28, and 22 are selected to achieve the required dc differences that produce the fields necessary to compensate for the effect of the waveform. For instance, in the above example the electrode 26 is biased −10 volts relative to electrodes 28 and 22. Of course, applying −5 volts to electrodes 26 and +5 volts to electrodes 28 achieves the same electric fields between electrodes 26 and 28. The balancing condition for the ion simply requires the 10 volt difference between the electrodes with correct polarization. Furthermore, the voltage difference between electrodes 26 and 28 and between 26 and 22 can also be selected. As noted above electrode 26 can be held at −5 volts and electrode 28 held at +5 volts. This suggests that the dc voltage applied to flat plate electrode 22 might be selected to push the ions toward electrodes 26 and pull the ions away from electrodes 28. A voltage of 0 volts applied to flat plate electrode 22 would have this effect. The voltage applied to flat plate electrode 22 must be established empirically by measurement of the efficiency of transport of ions carried by gas flow 42 through the analytical gap 20. At appropriate voltages applied to electrodes 26, 28 and 22, combined with the waveform applied to electrodes 26, the ion will approximately follow trajectory 44 through the analytical gap 20 between the electrode stack 24 and the flat plate electrode 22. The flow of gas 42 carries the ions along the analytical gap 20.

The ions tend to move to the focusing regions marked at 40, because of the attractive dc fields caused by the application of CV. The ions are carried out of the focusing region by the gas flow 42, and with appropriate voltages will move away from electrode 28. Once past electrode 28, the ion will begin to move towards the next electrode 26 in the electrode stack 24. This undulating motion continues as the ions traverse the analytical gap 20 between the electrode stack 24 and the flat plate electrode 22. Ions with other than a correct ratio of high field mobility to low field mobility suffer collisions with an electrode surface prior to being carried to the ion outlet 18. Although this discussion assumes a positive ion, with mobility that increases with electric field strength (recalling that field strength is being used to represent E/N), one of skill in the art will appreciate that the electrode arrangement shown in FIG. 1 can be used to separate negative ions and ions of either polarity whose mobility increases or decreases with E/N.

Figure 2B:
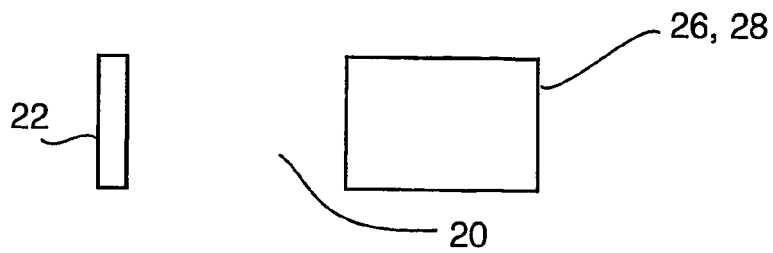
FIG. 2b is a simplified end view illustrating the shape of the electrodes of the stacked parallel plate FAIMS analyzer of FIG. 1.

Referring now to FIG. 2b, shown is a simplified end view illustrating the shape of the electrodes of the stacked parallel plate FAIMS analyzer of FIG. 1. Elements labeled with the same numerals have the same function as those illustrated in FIG. 1. The electrodes 26 and 28 preferably are approximately rectangular in shape when viewed from above, and have a width along an edge thereof adjacent to the gap 20. The flat plate electrode 22 is preferably of approximately a same width as the electrodes 26 and 28. The thickness of the flat plate electrode 22 is not a critical consideration provided there is a conductive surface.

Figure 2D:
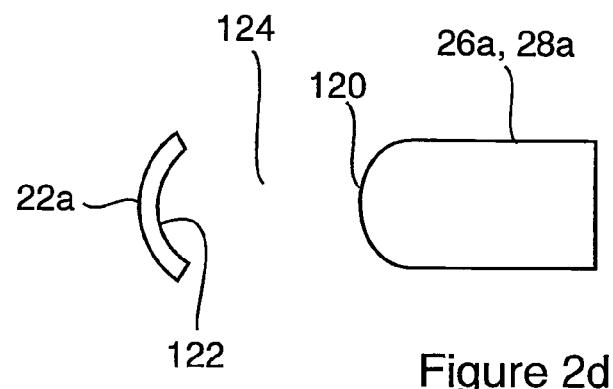
FIG. 2d is a simplified end view illustrating an alternative shape of the electrodes of the stacked parallel plate FAIMS analyzer of FIG. 1.
Figure 2C:
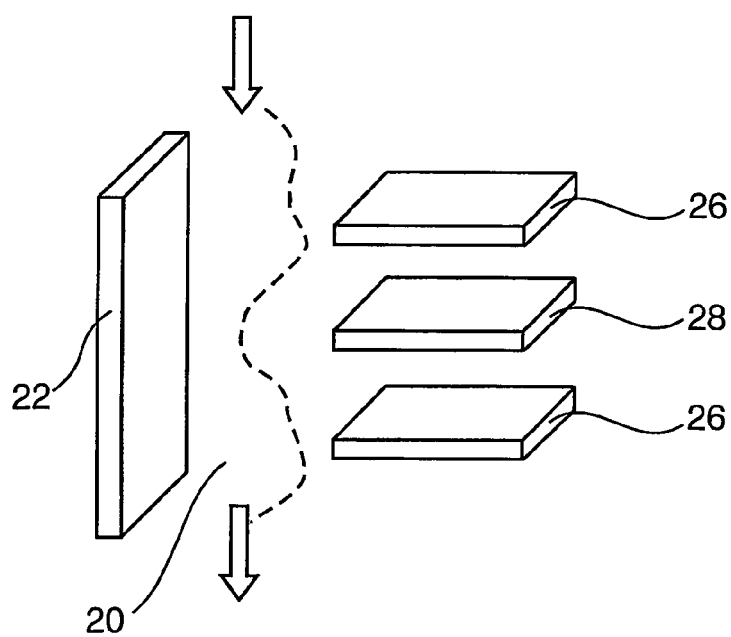
FIG. 2c is a simplified isometric view illustrating the shape of the electrodes of the stacked parallel plate FAIMS analyzer of FIG. 1.

Referring now to FIG. 2c, shown is a simplified isometric view illustrating the shape of the electrodes of the stacked parallel plate FAIMS analyzer of FIG. 1. Elements labeled with the same numerals have the same function as those illustrated in FIG. 1. As is evident from FIG. 2c, the electrodes 26 and 28 preferably have a thickness in a direction along the length of the stack 24 that is smaller than either the width or the length of the electrodes.

Referring now to FIG. 2d, shown is a simplified end view illustrating an alternative shape of the electrodes of the stacked parallel plate FAIMS analyzer of FIG. 1. Elements labeled with the same numerals have the same function as those illustrated in FIG. 1. Instead of having a flat edge adjacent to the analytical gap 124 as shown in FIG. 2b, the alternate shape electrodes 26a and 28a have a curved edge 120. An analytical gap 124 is defined between the curved edge 120 of the alternate shape electrodes 26a and 28a and a curved surface 122 of a curved plate electrode 22a. The three dimensional orientation of the alternate shape electrodes 26a and 28a relative to the curved plate electrode 22a is otherwise substantially similar to that shown at FIG. 2c.

Figure 2E:
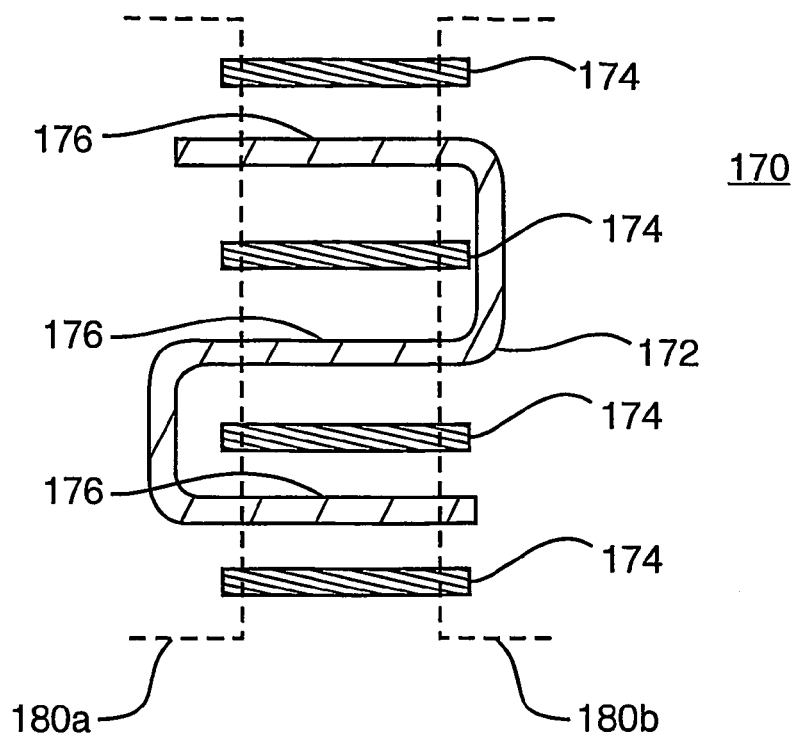
FIG. 2e shows a simplified cross sectional view of another FAIMS analyzer according to an embodiment of the instant invention, including a formed electrode.

Referring now to FIG. 2e, shown is a simplified cross sectional view of another FAIMS analyzer according to an embodiment of the instant invention and including a formed electrode. The FAIMS analyzer includes a not illustrated electrical controller that is connectable to an electrode assembly shown generally at 170 in FIG. 2e. The electrode assembly 170 includes a formed electrode in the form of a first electrode 172 including a first plurality of electrode portions 176 and a plurality of spaced-apart electrode plates 174. The first electrode 172 is embedded within an electrically insulating material 180a, 180b, such that the portions 176 of the first electrode 172 are disposed between and are electrically isolated from adjacent electrode plates 174.

For example, during use, at least an asymmetric waveform is applied to one of the first electrode 172 and the plurality of spaced-apart electrode plates 174. A dc voltage is applied to the other one of the first electrode 172 and the plurality of spaced-apart electrode plates 174. Additionally, a not illustrated electrode plate has a dc voltage applied to it, or is held at ground potential. The not illustrated electrode plate is spaced apart from the first electrode 172 and the plurality of spaced-apart electrode plates 174, so as to define an analytical gap between the not illustrated electrode plate and the first electrode 172 and the plurality of spaced-apart electrode plates 174. Of course, many other possible combinations of applying the dc voltages and the asymmetric waveform to the electrode assembly 170 will be apparent to one of skill in the art. It should be understood that the above example is intended to serve only as a specific and non-limiting example to facilitate a more complete understanding of the instant invention.

Figure 3A:
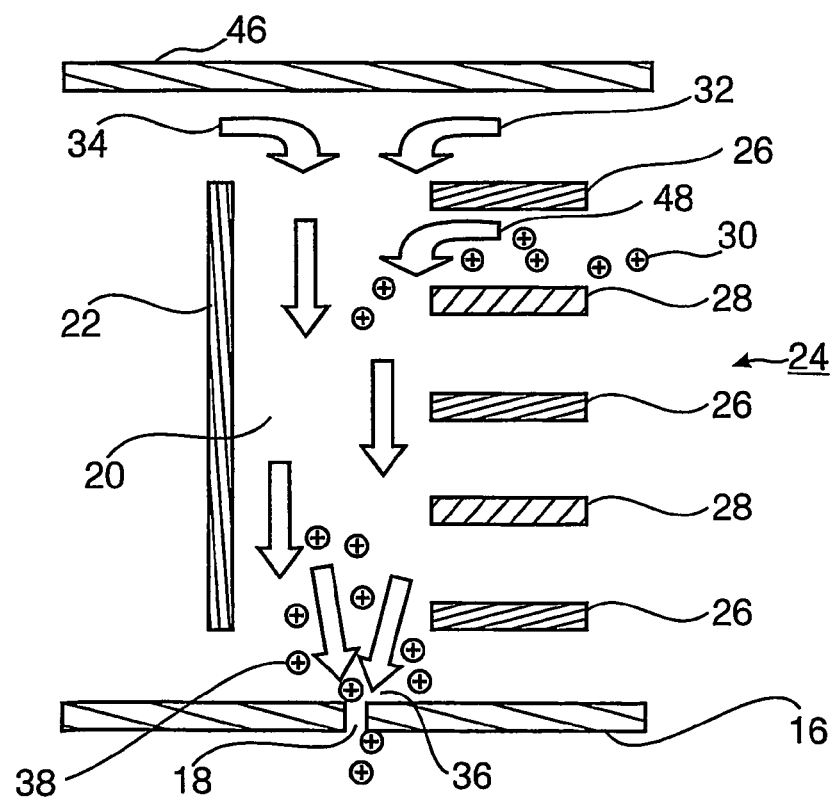
FIG. 3a is a simplified cross sectional view of another stacked parallel plate FAIMS analyzer according to an embodiment of the instant invention, in a first mode of operation.

Referring now to FIG. 3a, shown is a simplified cross sectional view of another stacked parallel plate FAIMS analyzer according to an embodiment of the instant invention. Elements labeled with the same numerals have the same function as those illustrated in FIG. 1. The stacked parallel plate FAIMS analyzer of FIG. 3a differs from the stacked parallel plate FAIMS analyzer 10 shown at FIG. 1 in that the ion inlet plate 12 with the ion inlet 14 is replaced with an endplate 46 absent an orifice. Accordingly, ions 30 are produced at a not illustrated ionization source and enter the stacked parallel plate FAIMS analyzer of FIG. 3a from between a pair of electrodes within the electrode stack 24. To this end, a flow of a gas 48 is provided from between the same pair of electrodes, so as to carry the ions 30 from the ionization source into the gap 20. The ions 30 pass along the analytical gap 20 between the electrode stack 24 and the flat plate electrode 22, as was described above with reference to FIG. 1. The gas. flows 32, 34, and 48 converge in a region 36 adjacent to the ion outlet 18, and exit the analytical gap 20 via the ion outlet 18. Advantageously, the ions 30 are carried predominantly through the analytical gap 20 between the flat plate electrode 22 and the electrode stack 24, and are channelled towards and through the ion outlet 18 as a result of the convergence of gas flows to the region 36 adjacent to the ion outlet 18. Since the stacked parallel plate FAIMS analyzer of FIG. 3a transports and separates ions based upon the FAIMS principle, only a sub-set 38 of the original mixture of ions 30 is transported to the ion outlet 18. Some of these selectively transported ions 38 pass through the ion outlet 18, and may be transported to one of an ion detection system, another ion mobility spectrometer, or alternatively to a mass spectrometer for further analysis.

The gas flows 32 and 34 are optionally replaced or augmented by a not shown orifice through the end plate 46. Preferably, at least a gas flow is provided along the length of the analytical gap 20 between the end plate 46 and the ion outlet 18, in order to more efficiently carry ions away from the edges of the electrode plates 26. In other words, the at least a gas flow disrupts the tendency of ions to become trapped within the electric fields that exist around the ends of the electrodes 26.

Figure 3B:
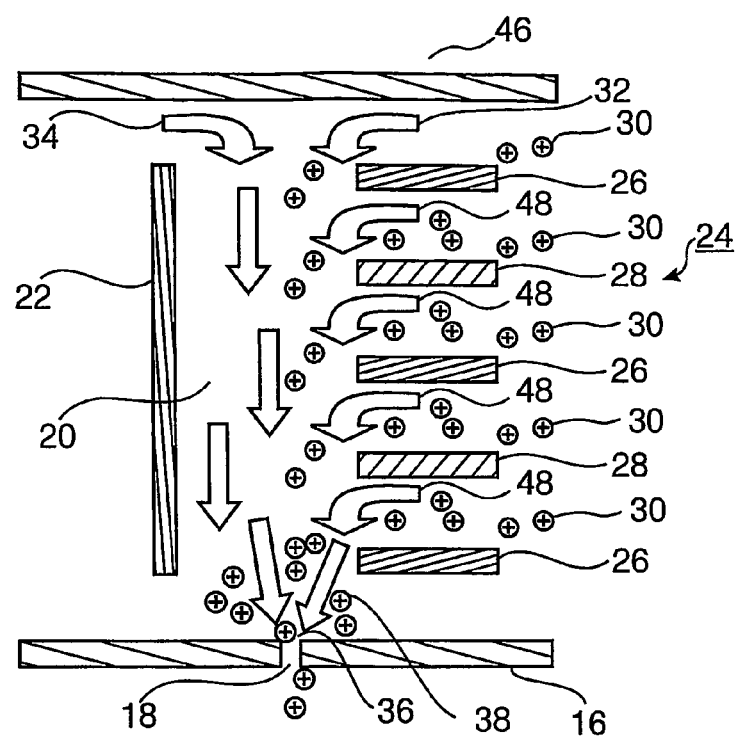
FIG. 3b shows the stacked parallel plate FAIMS analyzer of FIG. 3b in a second mode of operation.

Referring now to FIG. 3b, shown is the stacked parallel plate FAIMS analyzer of FIG. 3a in a second mode of operation. Elements labeled with the same numerals have the same function as those illustrated in FIG. 3a. In FIG. 3b, ions 30 from one or more ion sources are introduced into the analytical gap from between plural pairs of electrodes within the electrode stack 24. A gas flow 48 is also provided from between the plural pairs of electrodes, for carrying the ions 30 through the space between electrodes of the pairs of electrodes and into the analytical gap 20. Advantageously, the stacked parallel plate FAIMS analyzer when operated in a mode as shown in FIG. 3b provides an increased volume for separating ions compared to the above-mentioned embodiments. Accordingly, ion density within each space between pairs of electrodes may be reduced, such that ion loss as a result of ion-ion repulsion and space charge effects is reduced. Furthermore, ions that are other than of interest are lost to the electrodes during transit through the space between the pairs of electrodes, such that mostly ions of interest, for example ions comprising the subset 38 of the original mixture of ions 30, are transmitted into the analytical gap 20. Accordingly, the ion density introduced into the analytical gap 20 is reduced relative to a system in which ions produced at an ionization source are introduced directly into the analytical gap and the efficiency of the device as a collector is increased. Advantageously, the gas flows 32 and 34 through the analytical gap 20 serve to collect and transmit the ions of the subset of ions 38 from around the ends of the electrodes 26 and towards the ion outlet 18.

Optionally, one or both of the electrode stack 24 and the flat plate electrode 22 are moveable one relative to the other, so as to vary the size of the analytical gap 20 therebetween. Further optionally, non-uniform spacing is provided between facing surfaces of adjacent electrode plates within the electrode stack 24.

Optionally, the flat plate electrode 22 is provided as a conductive surface facing the analytical gap 20 that is applied to the not illustrated electrically insulating material. For instance, the conductive surface is a thin conductive layer deposited onto the not illustrated electrically insulating material using known techniques.

Optionally, a dc potential gradient is established along the length of the electrode stack such that an electrode 26 is, for example, one volt higher that the next occurring electrode 26 (along the ion flow path through the analytical gap 40). The alternating electrodes 28 mirror this pattern. This results in a CV between electrodes 26 and 28 that vary by ±1 volt from the standard operating mode and a CV between the flat plate electrode 22 and electrodes 26 that increases by 1 volt at the next occurring electrode 26. This causes the focusing region to move closer to the ends of the electrodes 26 along the length of the electrode stack. This may be desirable under specific circumstances.

Figure 4:
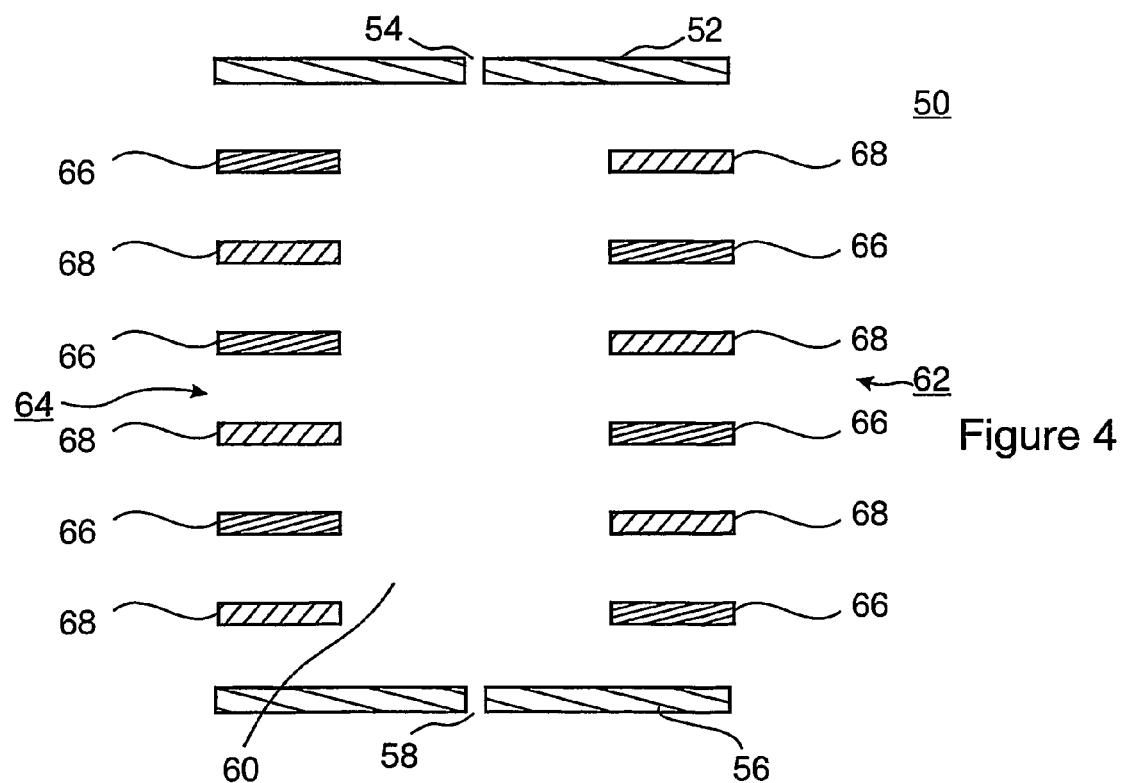
FIG. 4 is a simplified cross sectional view of still another stacked parallel plate FAIMS analyzer according to an embodiment of the instant invention.

Referring now to FIG. 4, shown is a simplified cross sectional view of another stacked parallel plate FAIMS analyzer according to an embodiment of the instant invention. The stacked parallel plate FAIMS analyzer, shown generally at 50, includes an ion inlet plate 52 with ion inlet 54, and an ion outlet plate 56 with ion outlet 58. A not illustrated electrically insulating material supports the plates 52 and 56 in a spaced-apart parallel arrangement. An analytical gap 60, which extends between the ion inlet plate 52 and the ion outlet plate 56, is defined between an edge of a first electrode stack 62 and a facing edge of a second electrode stack 64. Each one of the first electrode stack 62 and the second electrode stack 64 includes a plurality of electrode plates that are arranged, within a same stack, in a spaced-apart parallel arrangement relative to one another and relative to each one of the ion inlet plate 52 and the ion outlet plate 56. Of course, the electrically insulating material in which the plurality of electrode plates are supported has been omitted in FIG. 4 for the sake of clarity.

Individual electrode plates within each one of the first electrode stack 62 and the second electrode stack 64 are categorized into two different types of electrode plates 66 and 68, which are identified conveniently by the electric voltages applied to them by a not illustrated electrical controller. For example, each one of the electrode plates 66 has an asymmetric waveform and a dc compensation voltage applied to it; whilst each one of the electrode plates 68 has a dc voltage applied to it, or is held at ground potential. Optionally, different dc voltages are applied to one or more of the ion inlet plate 52, the ion outlet plate 56 and the electrode plates 68. Of course, many other possible combinations of applying the dc voltages and the asymmetric waveform to the electrode plates of the stacked parallel plate FAIMS analyzer 50 will be apparent to one of skill in the art. It should be understood that the above example is intended to serve only as a specific and non-limiting example to facilitate a more complete understanding of the instant invention.

The arrangement of the electrode plates 66 and 68 within each of the first electrode stack 62 and the second electrode stack 64 of the stacked parallel plate FAIMS analyzer 50 is important. Each electrode plate 66 is surrounded, above and below in FIG. 4, by a plate that does not carry the asymmetric waveform, for example one of the ion inlet plate 52, the ion outlet plate 56 and an electrode plate 68. Furthermore, the arrangement of the electrode plates 66 and 68 within the first electrode stack 62 is not identical to the arrangement of the electrode plates 66 and 68 within the second electrode stack 64. In FIG. 4, each one of the electrode plates 66 within the first electrode stack 62 is aligned with an electrode plate 68 within the second electrode stack 64. For clarity, two electrode plates disposed one each on opposite sides of the gap 60 are considered to be aligned one to the other when they are located a same vertical distance from ion inlet plate 52.

Figure 5:
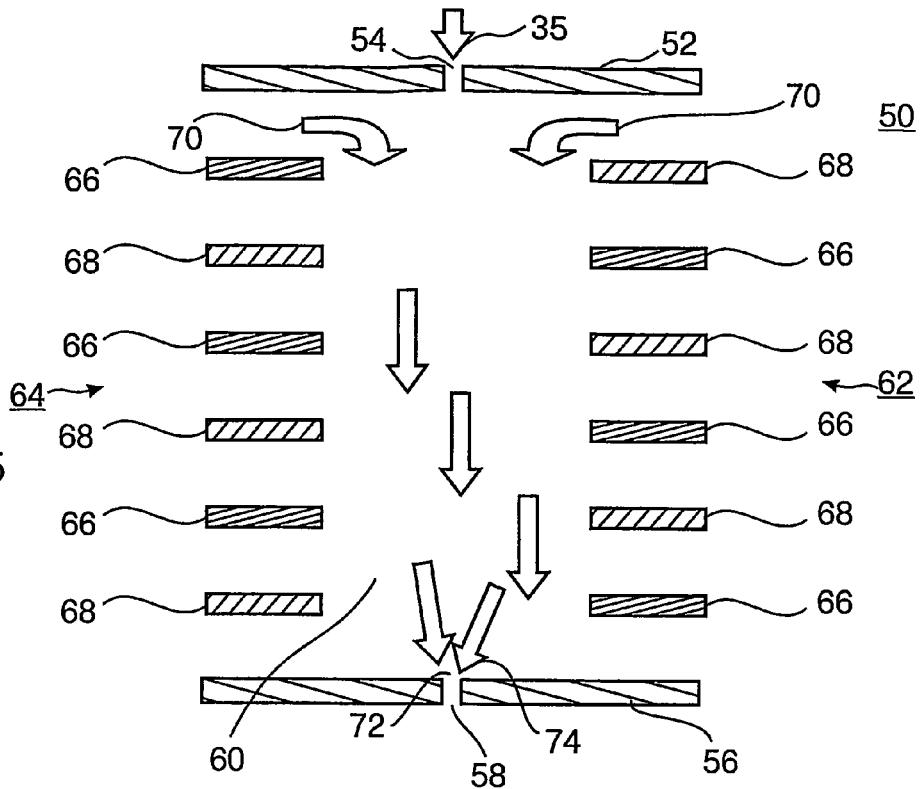
FIG. 5 shows an optional pattern of gas flow through the stacked parallel plate FAIMS analyzer of FIG. 4.

Referring now to FIG. 5, shown is a first optional pattern of gas flow through the stacked parallel plate FAIMS analyzer of FIG. 4. Elements labeled with the same numerals have the same function as those illustrated in FIG. 4. In this case, two streams of a gas flow 70 is provided from between the ion inlet plate 52 and the first and second electrode stacks 62 and 64, respectively. The two streams of the gas flow 70 converge in region 72 and the converged stream flows out of the ion outlet 58. In this way the ions are carried predominantly through the gap 60 between the first electrode stack 62 and the second electrode stack 64. Ions are channeled towards and through the ion outlet 58 because of the convergence of gas flows 74 to this location. Optionally, a gas flow 70 is provided from between all of the pairs of electrodes in first electrode stack 62 and the second electrode stack 64.

Figure 6:
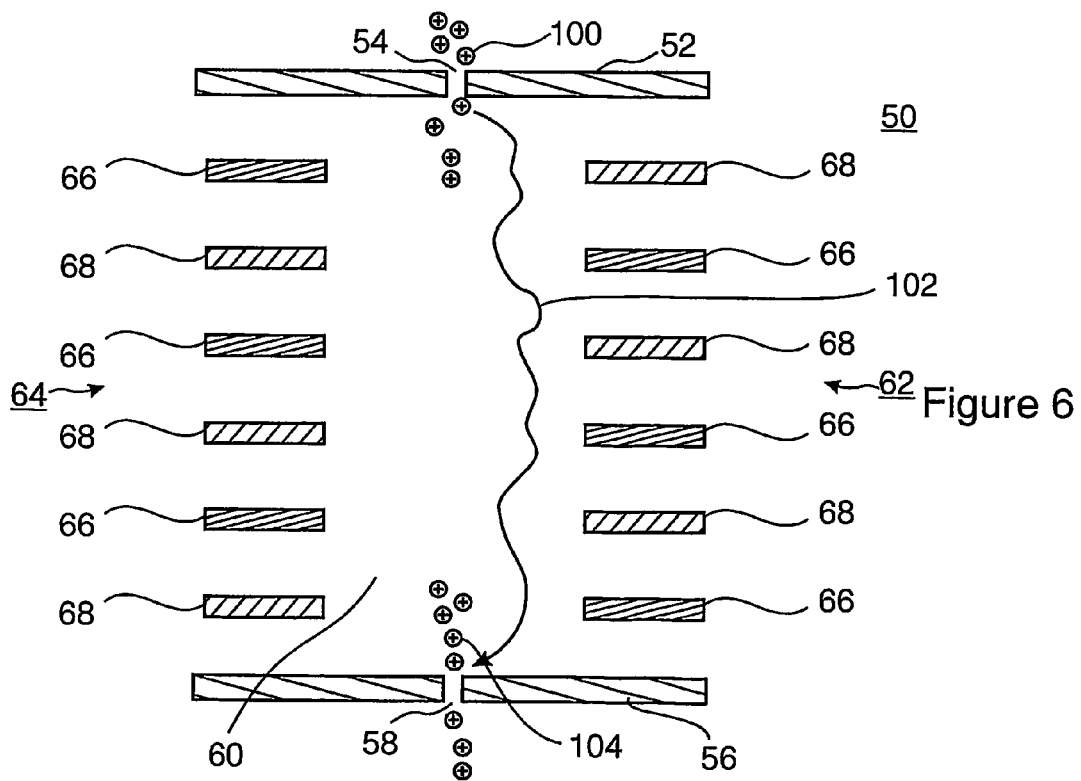
FIG. 6 illustrates an example of an ion trajectory through the stacked parallel plate FAIMS analyzer of FIG. 4.

Referring now to FIG. 6, shown is an example of an ion trajectory through the stacked parallel plate FAIMS analyzer of FIG. 4. Elements labeled with the same numerals have the same function as those illustrated in FIG. 4. Ions 100 are produced at a not illustrated ionization source and enter the stacked parallel plate FAIMS analyzer 50 through the ion inlet 54 in the ion inlet plate 52. The ions 100 follow various trajectories through the analytical gap 60 between the ion inlet 54 and the ion outlet 58. One hypothetical ion trajectory is represented by the solid line 102 in FIG. 6. Since the device 50 operates on the basis of the FAIMS principle, only those ions 104 whose trajectory through the analytical gap 60 is stable for a given combination of applied DV and CV are transmitted to the ion outlet 58. The ions 104 represent a sub-set of all of the types of ions 100 entering the device 50, namely those ions with the appropriate ratio of high field mobility to low field mobility. Some of these selectively transported ions 104 pass through the ion outlet 58, and may be transported to one of an ion detection system, another ion mobility spectrometer, or alternatively to a mass spectrometer for further analysis.

Figure 7:
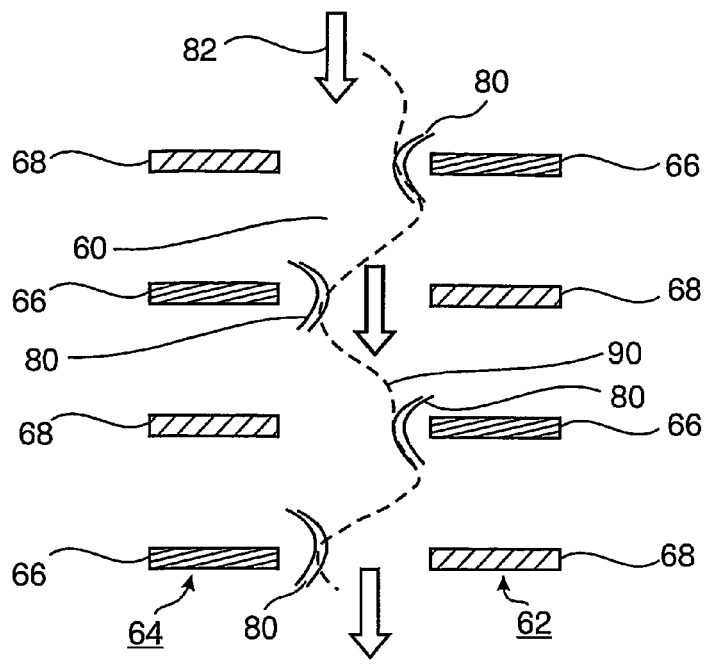
FIG. 7 illustrates the effect of electric fields within the stacked parallel plate FAIMS analyzer of FIG. 4 on the trajectory of an ion.

Referring now to FIG. 7, shown is a schematic representation of the effect of the electric fields within the stacked parallel plate analyzer 50 of FIG. 4 on the trajectory of an ion. Elements labeled with the same numerals have the same function as those illustrated in FIG. 4. As was described with reference to FIG. 4 above, the asymmetric waveform and dc compensation voltage is applied to electrode plates 66, and a dc voltage (or optionally ground potential) is applied to electrode plates 68. The electric fields between the electrode plates 66 and 68 comprise a variable (asymmetric waveform) component and a constant dc (in time) component. The application of the asymmetric waveform results in an electric field that is stronger in one polarity than in the other. Since the mobility of the ion may be higher or lower in the stronger field than in the lower field of opposite polarity, the oscillation of the ion may cause it to drift towards one of the electrodes. The dc component of the electric field is applied in order to counteract, or compensate, for this drift. Under the correct combination of asymmetric waveform and applied dc voltage difference between the electrode plates, ions with an appropriate ratio of mobility at high field to mobility at low field are in a balanced condition. In other words, the drift effect caused by the electric field arising from the applied CV just matches the drift effect caused by application of the waveform with peak voltage DV.

The electric field between electrodes 66 and 68 is constant in space, i.e. uniform between the electrodes. However, the electric field between electrodes 66 and 68 begins to change near the edges of the electrodes. The field at the edge of each electrode 66 varies in strength with distance away from the edge and extends into the analytical gap 60. The application of the DV and the CV combined with the non-uniform field at the edge results in an ion-focusing region 80 proximate to electrode 66 in which ions maintain their balanced condition. That is to say, at distances very close to the edge of electrode 66 where the field is strong the ions migrate away from the electrode 66 to the region 80, and at positions in the analytical gap 60 where the field is weaker the ions migrate towards the electrode 66 to region 80. Ions are extracted from region 80 under the influence of, for example, a gas flow 82 or a potential gradient along the length of the electrode stacks 62 and 64.

Accordingly, the ions travel through the analytical gap 60 with trajectories having characteristics such as that shown as 90 in FIG. 7. When the ion is between electrodes 66 and 68 of facing electrode stacks, the ion will prefer to be located at the focus area 80. If the ion is carried from between one pair of facing electrodes 66 and 68 to the next adjacent pair by the flow of gas 82, the electrodes have effectively "switched sides" and the new optimum focus region 80 is now on the other side of the analytical gap 60 between the stacks of electrodes 62, 64. The ion therefore undulates from one side of the analytical gap 60 to the other as it is carried by gas flow 82. The progression of ion flow from one focusing region to the next maximizes ion transmission efficiency through the analytical gap 60.

The ion trajectory 90 shown in FIG. 7 suggests that alternative methods for applying the dc voltages to the electrodes 66, 68 can be visualized. For example, the CV, which creates the dc fields between electrodes 66 and 68, can be distributed between electrodes 66 and 68. In the example above, all of the CV, for example a dc voltage of −10 volts, was superimposed on the waveform applied to electrodes 66 while electrodes 68 were kept at ground potential. Alternatively, a dc voltage of −5 volts is applied to electrodes 66 superimposed on the waveform, and electrodes 68 are biased to +5 volts. The net difference of 10 volts and the proper polarity between electrodes 66 and 68 is maintained.

Optionally, a dc voltage gradient is created along the length of the electrode stacks 62, 64. In this case, a first voltage gradient along the length of the electrodes is introduced by an offset in dc voltage from layer to layer along the stack. For example at the first layer, both aligned electrodes 68 and 66 are held at +10 volts. At the next layer, both aligned electrodes 66 and 68 (in opposite order than in the previous layer) are held at +9 volts. This imposes a 1 volt difference between layers, and therefore a field along the length of the electrode stacks 62, 64. Each subsequent layer is also biased 1 volt lower (for example) relative to the previous layer. However, further voltages must be superimposed on the dc voltages that are described above to create a FAIMS system. For example, when an asymmetric waveform is applied to the electrodes 66, a selected ion cannot be transmitted under the above-described conditions because a compensating field does not exist to counteract the migration of the ion towards one of the electrodes as a result of the ion mobility in the alternating strong and weak fields thereby created. Fortunately, the CV is not defined by an absolute voltage, but rather as a difference in voltages between the electrodes 66 and 68. For example, for ion transmission to occur each electrode 66 must be 10 volts more negative than each electrode 68 or alternately stated a dc voltage difference of 10 volts in the right polarity must exist between each electrode 66 and 68. Of course, the actual value of the CV required to establish a balanced condition is always dependent upon an ion identity as well as a number of operating conditions. In order to apply both a voltage gradient along the length of the electrode stacks 62, 64 as well as the desired compensation voltage a compromise condition results where the CV between electrodes 66 and 68 within a stack vary, in this example, by ±1 volt from the CV of 10 volts between aligned electrodes. The dc compensation field cannot be identical on both sides of each plate since a fixed voltage difference (to create the gradient) is superimposed on the requirement for a compensation voltage.

Optionally, the electrode stacks 62 and 64 are moveable one relative to the other, so as to vary the size of the analytical gap 60 therebetween. Further optionally, non-uniform spacing is provided between facing surfaces of adjacent electrode plates within a same electrode stack. Still further optionally, ions are provided from between one or more pairs of electrodes in either or both of the electrode stacks 62 and 64, in a manner similar to that described with reference to FIGS. 3a and 3b above.

Figure 8A:
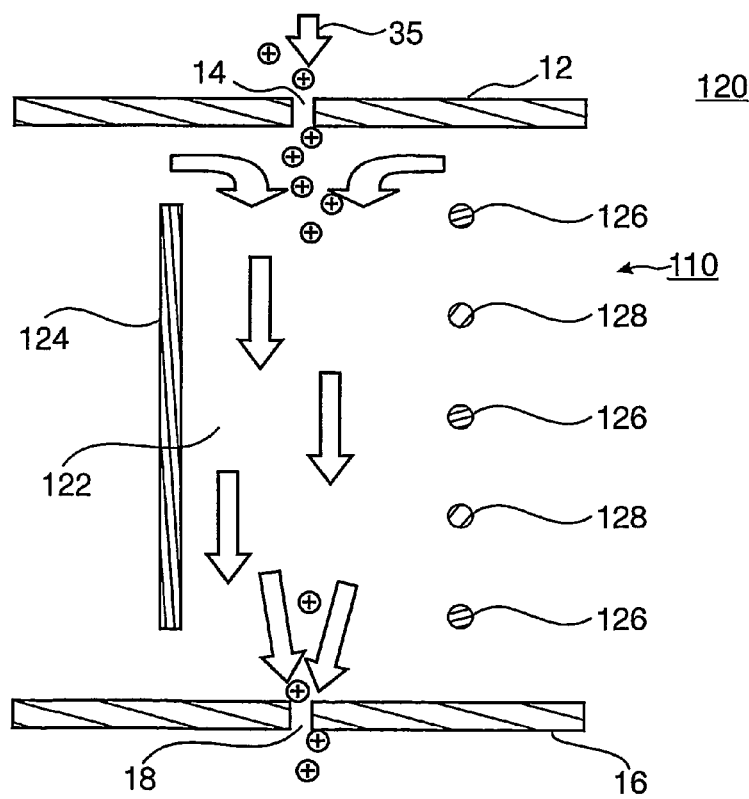
FIG. 8a is a simplified cross sectional view of another stacked electrode FAIMS analyzer according to an embodiment of the instant invention.

Referring now to FIG. 8a, shown is a simplified cross sectional view of another stacked electrode FAIMS analyzer according to an embodiment of the instant invention. In FIG. 8a, the electrode stack 24 of the stacked parallel plate FAIMS analyzer 10 of FIG. 1 is replaced with an electrode stack 110 including a plurality of spaced-apart parallel wires or rods. The stacked electrode FAIMS analyzer, shown generally at 120, includes an ion inlet plate 12 with an ion inlet 14, and an ion outlet plate 16 with an ion outlet 18. A not illustrated electrically insulating material supports the plates 12 and 16 in a spaced-apart parallel arrangement. An analytical gap 122, which extends between the ion inlet plate 12 and the ion outlet plate 16, is defined between the electrode stack 110 and a facing surface of a flat plate electrode 124. The electrode stack 110 includes individual wires or rods that are arranged in a spaced-apart parallel arrangement relative to one another and relative to each one of the ion inlet plate 12 and the ion outlet plate 16. Each wire or rod is either made from conducting material or has a conducting surface layer. Of course, the electrically insulating material in which the plurality of spaced-apart parallel wires or rods 110 and the flat plate electrode 124 are supported has been omitted in FIG. 8a for the sake of clarity.

The individual spaced-apart parallel wires or rods are categorized into two different electrodes 126 and 128, which are identified conveniently by the electric voltages applied to them by a not illustrated electrical controller. For example, each one of the electrodes 126 has an asymmetric waveform and a dc compensation voltage applied to it; whilst each one of the electrodes 128 has a dc voltage applied to it, or is held at ground potential. Additionally, the flat plate electrode 124 has a dc voltage applied to it, or is held at ground potential. Optionally, different dc voltages are applied to one or more of the ion inlet plate 12, the ion outlet plate 16 and the flat plate electrode 124. Of course, many other possible combinations of applying the dc voltages and the asymmetric waveform to the electrodes of the stacked electrode FAIMS analyzer 120 will be apparent to one of skill in the art. It should be understood that the above example is intended to serve only as a specific and non-limiting example to facilitate a more complete understanding of the instant invention.

Figure 8B:
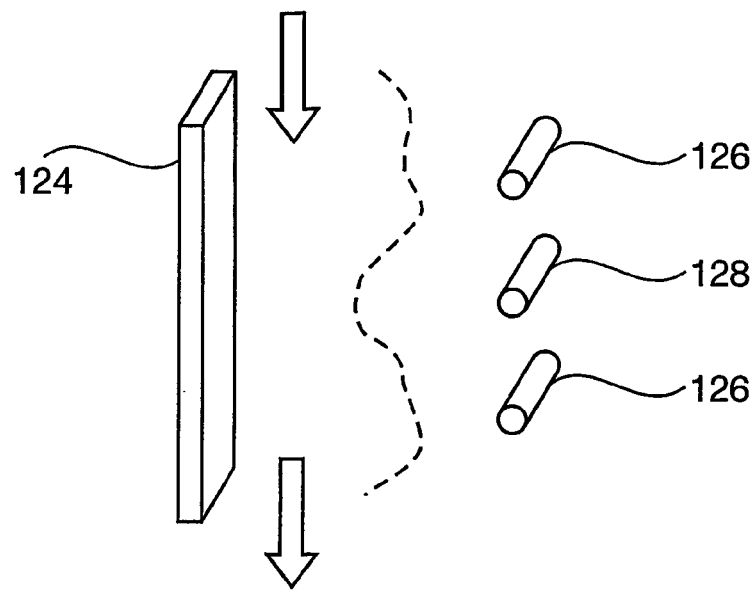

FIG. 8b is a simplified isometric view illustrating the shape of the electrodes of the stacked electrode FAIMS analyzer of FIG. 8a. Elements labeled with the same numerals have the same function as those illustrated in FIG. 8a.

Figure 9A:
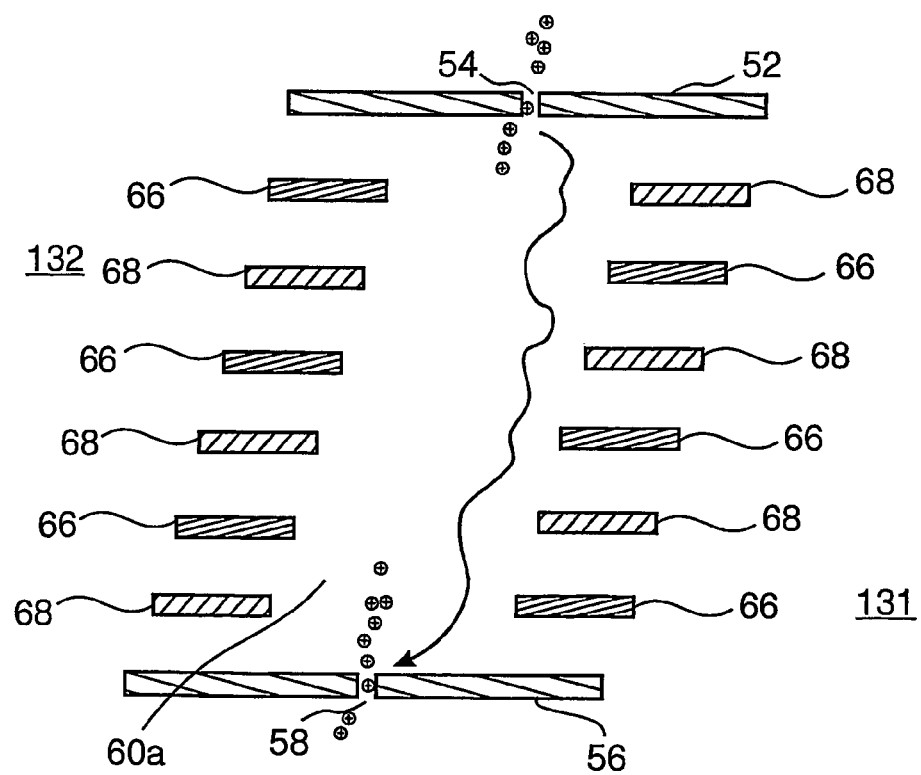
FIG. 9a shows an optional electrode arrangement of the stacked parallel plate FAIMS analyzer of FIG. 4.

FIG. 9a shows an optional electrode arrangement of the stacked parallel plate FAIMS analyzer of FIG. 4. The stacked parallel plate FAIMS analyzer, shown generally at 130, has an electrode arrangement in which adjacent electrode plates within each a same stack are offset slightly in a regular fashion in a direction transverse to a length of the stack. Accordingly, the edges of the electrode stacks remain aligned, i.e. the edges of the electrode plates within a stack define a straight line and define an analytical gap 60a that is of approximately uniform width. The angle of alignment of this optional electrode arrangement relative to the ion inlet plate is no longer 90 degrees.

Of course, any of the embodiments described supra are optionally modified in a manner similar to that shown in FIG. 9a. Further optionally, specifically for those embodiments having a flat plate electrode instead of a second stack, the flat plate electrode is replaced with an electrode plate that is curved in a direction along the length of the electrode. In addition, the electrode plates of an electrode stack adjacent to the curved electrode plate are disposed at a distance from the curved plate electrode so as to maintain a substantially uniform spacing therebetween.

Figure 9B:
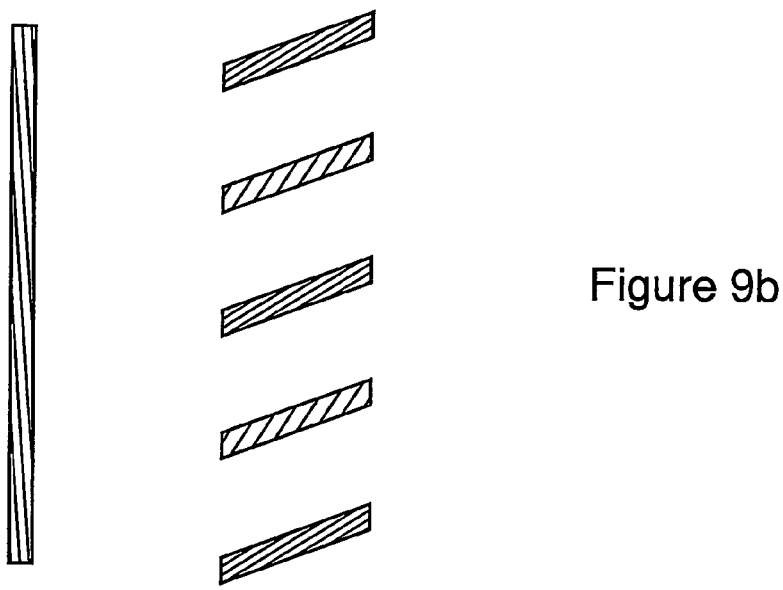
FIG. 9b shows an optional electrode arrangement of the stacked parallel plate FAIMS analyzer of FIG. 1.

Referring now to FIG. 9b, shown is an optional electrode arrangement of the stacked parallel plate FAIMS analyzer of FIG. 1. The electrode plates are arranged parallel one relative to another, but are not perpendicular to the flat plate electrode.

Figure 10:
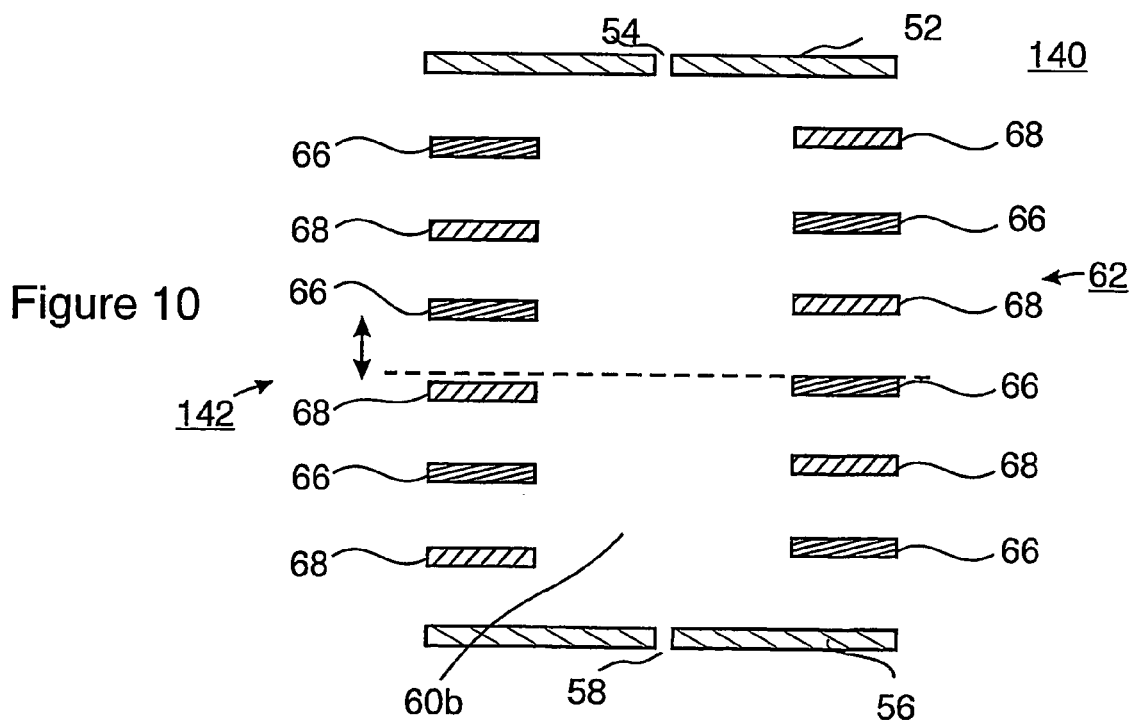
FIG. 10 shows the stacked parallel plate FAIMS analyzer of FIG. 4 with an adjustable electrode stack.

Referring now to FIG. 10, shown is the stacked parallel plate FAIMS analyzer of FIG. 4 with a vertically adjustable electrode stack. The adjustable electrode stack, shown in FIG. 10 at 142, is relatively moveable in a direction towards at least one of the ion inlet plate 52 and the ion outlet plate 56. Moving the adjustable electrode stack 142 relative to the other electrode stack 62 results in a small offset between aligned plates, as indicated by the dotted line in FIG. 10. This offset can be used to perturb the electric fields within the analytical gap 60b so as to empirically optimize ion transmission through the device.

Figure 11:
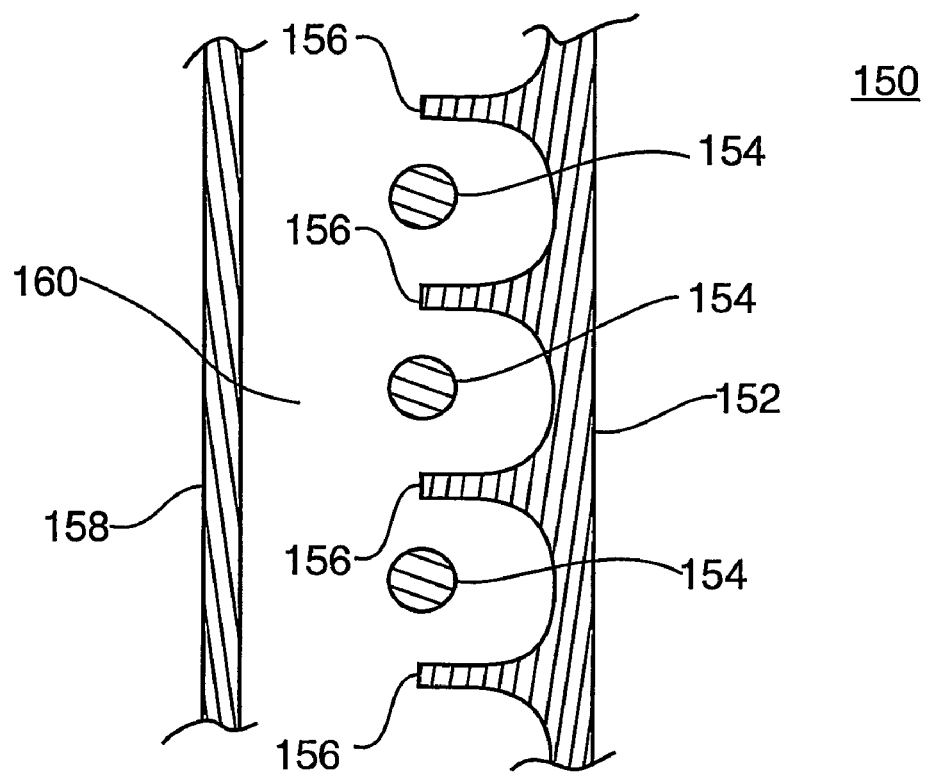
FIG. 11 shows a simplified cross sectional view of a FAIMS analyzer according to an embodiment of the instant invention, including a formed electrode.

Optionally, a formed electrode replaces at least some of the electrodes within an electrode stack. Referring now to FIG. 11, shown is a simplified cross sectional view of a FAIMS analyzer according to an embodiment of the instant invention and including a formed electrode. The FAIMS analyzer includes a not illustrated electrical controller that is connectable to an electrode assembly shown generally at 150 in FIG. 11. The electrode assembly 150 includes a formed electrode in the form of a first electrode 152 including a first plurality of electrode portions, for instance protrusions 156. The electrode assembly 150 further includes a plurality of spaced-apart rods or wires 154. Each rod or wire 154 of the plurality of rods or wires is arranged in an alternating sequence with the plurality of electrode portions 156 of the first electrode 152, as shown in FIG. 11. In particular, one rod or wire 154 of the plurality of rods or wires is disposed within a space between two adjacent protrusions 156 of the first electrode 152, and is supported by a not illustrated electrically insulating material. A portion of each rod or wire 154 between two adjacent protrusions 156 of the first electrode 152 is not embedded within the electrically insulating material. As is shown in FIG. 11, the centre of each rod or wire 154 is aligned with a terminal edge of each protrusion 156 within an analytical gap 160, which is defined by a space between the first electrode 152 and an electrode plate 158. Optionally, each rod or wire 154 is displaced in a direction toward the electrode plate 158 Collectively, the portion of each rod or wire 154 of the plurality of rods or wires comprises a second electrode in the form of a second plurality of electrode portions. Furthermore, each rod or wire 154 of the plurality of rods or wires is in electrical communication with the electrical controller for receiving at least an asymmetric waveform voltage.

The electrode plate 158 and the formed electrode 152, which form a part of the electrode assembly 150, are in electrical communication with the electrical controller for receiving direct current voltages, or optionally are held at ground potential. The dc voltages are selected to create ion focusing regions in the vicinity of each rod or wire 154. Ions having appropriate high field mobility properties for a given combination of applied asymmetric waveform voltage and dc voltage are selectively transmitted within the analytical gap 160 between an ion inlet end and an ion outlet end thereof.

Of course, many other possible combinations of applying the dc voltages and the asymmetric waveform to the electrode assembly 150 will be apparent to one of skill in the art. It should be understood that the above example is intended to serve only as a specific and non-limiting example to facilitate a more complete understanding of the instant invention.

Figure 12:
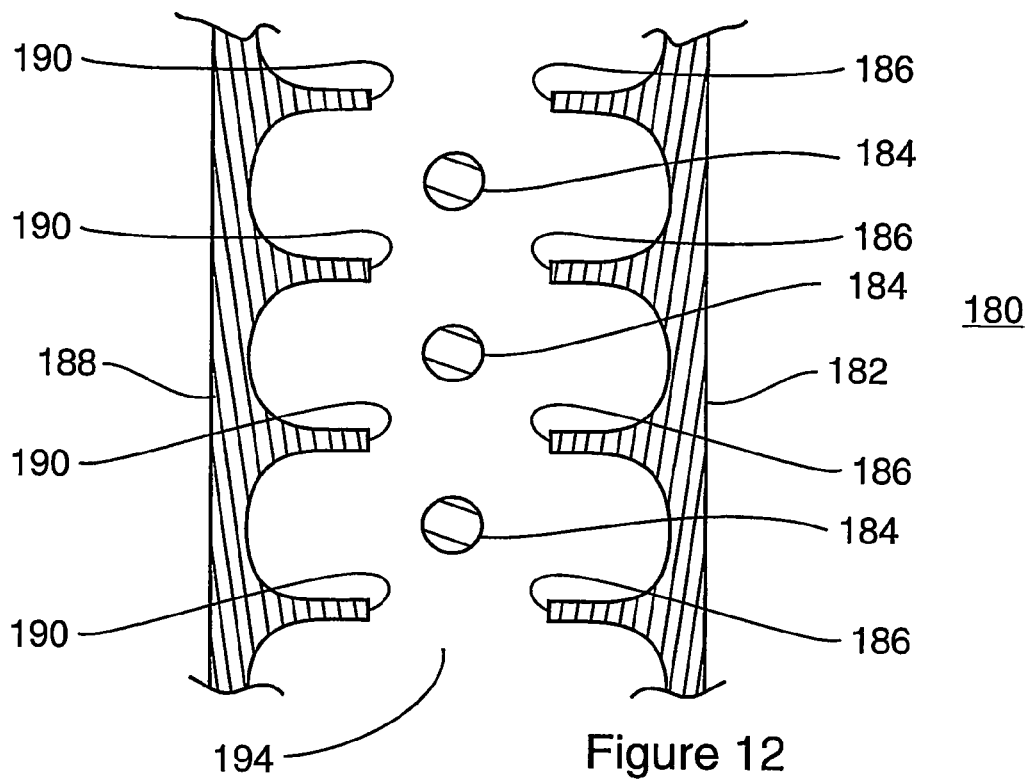
FIG. 12 shows a simplified cross sectional view of a FAIMS analyzer according to an embodiment of the instant invention, including two formed electrodes.

Referring now to FIG. 12, shown is a simplified cross sectional view of a FAIMS analyzer according to an embodiment of the instant invention and including two formed electrodes. The FAIMS analyzer includes at least a not illustrated electrical controller for being electrically coupled to an electrode assembly shown generally at 180 in FIG. 12. The electrode assembly 180 includes a first formed electrode in the form of a first electrode 182 including a first plurality of electrode portions, for instance a plurality of protrusions 186. The first electrode 182 is electrically coupled to an electrical controller of the at least an electrical controller for receiving a dc voltage. The electrode assembly 180 further includes a second formed electrode in the form of a second electrode 188 including a second plurality of electrode portions, for instance a plurality of protrusions 190. The second electrode 188 is provided in a spaced apart facing arrangement with the first electrode 182, defining an analytical gap 194 therebetween. The second electrode 188 is electrically coupled to an electrical controller for receiving a dc voltage. Each protrusion 186 of the first electrode 182 is aligned with a protrusion 190 of the second electrode 188. In addition, the electrode assembly 180 includes a plurality of spaced-apart rods or wires. Each rod or wire 184 of the plurality of rods or wires is disposed within the analytical gap 194 between the first and second electrodes 182 and 188, respectively. Preferably, the centre of each rod or wire 184 is disposed at point that is approximately midway between two pairs of adjacent protrusions in a longitudinal direction and midway between the first and second electrodes 182 and 188 in a transverse direction. Each rod or wire 184 of the plurality of rods or wires is supported by a not illustrated electrically insulating material. Each rod or wire 184 of the plurality of rods or wires is electrically coupled to an electrical controller for receiving an asymmetric waveform voltage and optionally a dc voltage.

As mentioned above, the space between the first electrode 182 and the second electrode 188 defines an analytical gap 194 for allowing ions to propagate therethrough. Ions having appropriate high field mobility properties for a given combination of applied asymmetric waveform voltage and CV are selectively transmitted within the analytical gap 194 between an ion inlet end and an ion outlet end thereof. Of course, many other possible combinations of applying the dc voltages and the asymmetric waveform voltage to the electrode assembly 180 will be apparent to one of skill in the art.

It should be understood that the above example is intended to serve only as a specific and non-limiting example to facilitate a more complete understanding of the instant invention. It is important, however, that each electrode portion to which an asymmetric waveform is applied is surrounded above, below and to the side with electrode portions to which only a dc voltage is applied. For example, the asymmetric waveform voltage is applied to the first and second electrodes 182 and 188 and not to the rods or wires 184.

Figure 13:
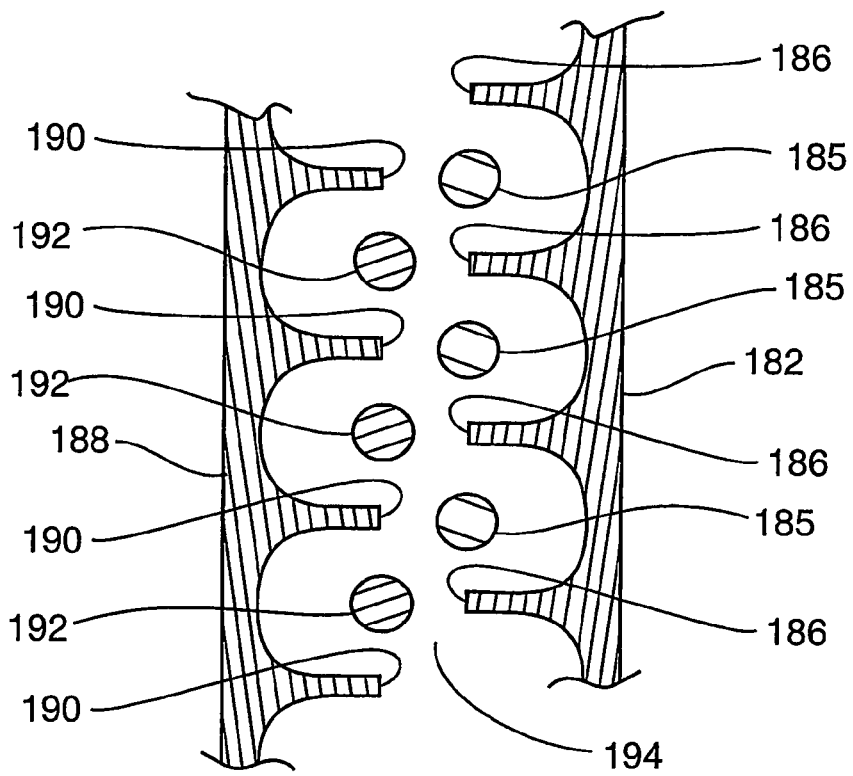
FIG. 13 shows a simplified cross sectional view of another FAIMS analyzer according to an embodiment of the instant invention, including two formed electrodes; and, FIG. 14 shows a simplified flow diagram for a method of separating ions according to an embodiment of the instant invention.

Referring now to FIG. 13, shown is another FAIMS analyzer according to an embodiment of the instant invention and including two formed electrodes. Elements labelled with the same numerals have the same functions as those elements shown at FIG. 12. In FIG. 13, the first electrode 182 is shifted relative to the second electrode 188 such that the protrusions 186 of the first electrode 182 are other than aligned with the protrusions 190 of the second electrode 188. Accordingly, the asymmetric waveform must be applied to the first electrode 182 and the second electrode 188 in FIG. 13. A direct current voltage is applied to rods or wires of each one of a first plurality of rods or wires 185 and a second plurality of rods or wires 192.

Figure 14:
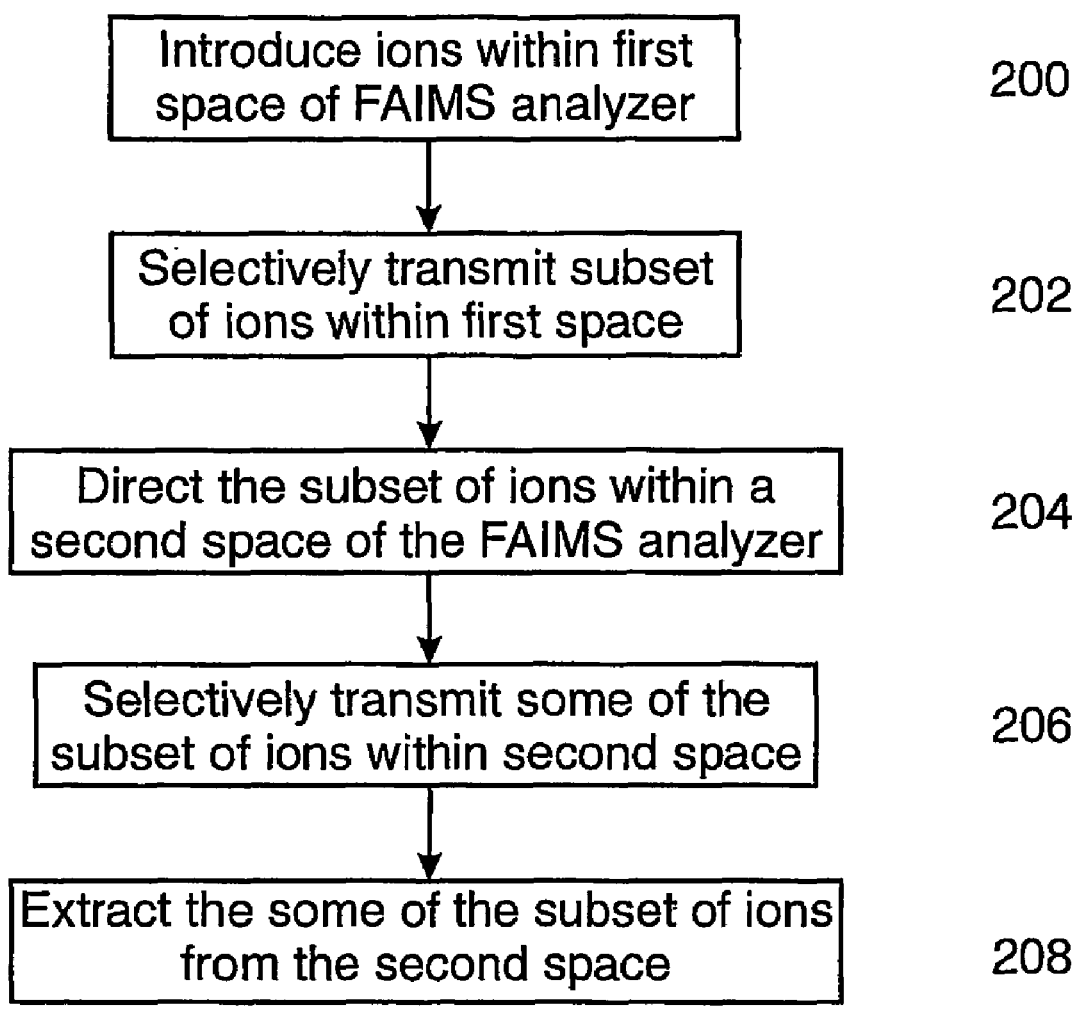

Referring now to FIG. 14, shown is a simplified flow diagram for a method of separating ions according to the instant invention. At step 200, ions are introduced into a first space defined between adjacent electrode plates of a stacked parallel plate high field asymmetric waveform ion mobility spectrometer (FAIMS). At step 202, a subset of the ions is selectively transmitted in a first direction through the first space as a result of a particular combination of applied asymmetric waveform and dc compensation voltage. In other words, a first separation of the ions is performed within the first space. At step 204, the subset of the ions is directed along a second space in a second direction approximately transverse to the first direction. At step 206, some of the subset of ions is selectively transmitted through the second space towards an ion outlet. In other words, a second separation of the ions is performed within the second space. The some of the subset of the ions are subsequently extracted at step 208 for detection or further analysis.

Of course, different configurations of an electrical controller are envisaged as options for providing the asymmetric waveform voltage and the CV. Power sources may be combined in one housing or may be in the form of separately housed components. The electrical controller may include an electronic circuit, for instance to generate the asymmetric waveform, or may be a simple device such as an electrically conducting wire for maintaining an electrode at ground potential. The term electrical controller has been used to denote the means by which a desired voltage is applied and maintained on an electrode. Although the foregoing detailed description of the instant invention describes electrical voltages as being applied to specific electrodes of the various electrode assemblies, for example via electrical contacts carried on the specific electrodes, it is to be understood that the effect is to apply a desired voltage between electrodes so as to establish an electrical field for separating the ions. Of course, the strength of the electric field that is established is dependent upon the voltages that are applied between the electrodes, as well as the distance between the electrodes that are used to establish the fields.

It is an advantage of some embodiments of the instant invention that higher resolution is achieved relative to prior art devices. For instance, a first CV may be applied to separate a subset of the ions within a first portion of the device according to the instant invention, followed by application of a second different CV to transmit a smaller subset of the ions within a second portion of the device according to the instant invention.

Numerous other embodiments may be envisaged without departing from the spirit and scope of the invention.

What is claimed is:

1. An apparatus for separating ions comprising:
   an electrode stack having a length defined along a stacking direction and comprising a plurality of electrodes, each electrode of the electrode stack being spaced apart from an adjacent electrode of the electrode stack along the stacking direction, each electrode of the electrode stack having an edge defining a portion of an edge of the electrode stack;
   at least an electrode spaced apart from the edge of the electrode stack in a direction transverse to the stacking direction, the space between the at least an electrode and the edge of the electrode stack defining an analytical gap for allowing ions to propagate therebetween along the stacking direction;
   an ion outlet plate disposed adjacent to a first end of the electrode stack and spaced-apart from the electrode stack along the stacking direction the ion outlet plate defining an ion outlet for extracting from the analytical gap ions propagating along the stacking direction; and,
   at least an electrical controller for electrically coupling to at least one of an electrode of the plurality of electrodes of the electrode stack and the at least an electrode, for applying an asymmetric waveform voltage between the electrode of the plurality of electrodes of the electrode stack and the at least an electrode and for applying a direct current voltage between the electrode of the plurality of electrodes of the electrode stack and the at least an electrode so as to establish an electric field within the analytical gap.

2. An apparatus according to claim 1, wherein the edge of each electrode of the electrode stack is approximately aligned with an edge of every other electrode of the electrode stack so as to define the edge of the electrode stack.

3. An apparatus according to claim 1, wherein a spacing between any two adjacent electrodes of the electrode stack is approximately a same spacing.

4. An apparatus according to claim 1, wherein each electrode of the electrode stack comprises an electrode plate.

5. An apparatus according to claim 1, wherein each electrode of the electrode stack comprises an electrode rod.

6. An apparatus according to claim 1, wherein the electrode stack is relatively moveable in a direction toward the at least an electrode, such that a width of the analytical gap is controllably variable.

7. An apparatus according to claim 1, wherein the at least an electrode comprises an electrode plate having a length and being oriented so as to maintain an approximately uniform spacing along the length of the electrode plate to the edge of the electrode stack.

8. An apparatus according to claim 7, wherein the electrode plate is curved in a direction along the length of the electrode plate.

9. An apparatus according to claim 7, wherein the electrode plate is curved in a direction transverse to length of the electrode plate.

10. An apparatus according to claim 1, wherein the at least an electrode comprises a second electrode stack having a length, the length of the second electrode stack being substantially similar to the length of the electrode stack.

11. An apparatus according to claim 10, wherein the second electrode stack comprises a plurality of electrodes, each electrode of the second electrode stack being spaced apart from an adjacent electrode of the second electrode stack in a direction along the length of the second electrode stack, each electrode of the second electrode stack having an edge defining a portion of an edge of the second electrode stack.

12. An apparatus according to claim 11, wherein the edge of each electrode of the second electrode stack is aligned with an edge of every other electrode of the second electrode stack so as to define the edge of the second electrode stack.

13. An apparatus according to claim 11, wherein the second electrode stack is disposed such that the edge of the second electrode stack faces the edge of the electrode stack in a spaced apart arrangement, the space between the edge of the second electrode stack and the edge of the electrode stack defining the analytical gap.

14. An apparatus according to claim 10, wherein the second electrode stack is moveable relative to the first electrode stack in a direction along the length of the second electrode stack.

15. An apparatus according to claim 1, comprising an ion inlet plate disposed adjacent to a second end of the electrode stack opposite the first end and spaced-apart from the electrode stack along the stacking direction, the ion inlet plate and defining an ion inlet for introducing ions into the analytical gap.

16. An apparatus according to claim 1, comprising an ion inlet for introducing ions into the analytical gap via a space between at least an electrode of the electrode stack and an adjacent electrode of the electrode stack.

17. An apparatus according to claim 16, comprising a gas inlet for introducing a flow of a gas into the analytical gap for carrying the ions in a direction towards the ion outlet.

18. An apparatus according to claim 17, wherein the gas inlet is disposed at a point that is more distal from the ion outlet relative to the ion inlet.

19. An apparatus for separating ions comprising:
    an electrode assembly including;
    at least a first electrode comprising a first plurality of electrode portions;
    at least a second electrode comprising a second plurality of electrode portions arranged in alternating sequence with the first plurality of electrode portions along a first direction;
    an electrode plate spaced apart from the first plurality of electrode portions and the second plurality of electrode portions in a second direction transverse to the first direction, the space between the electrode plate and the first plurality of electrode portions and the second plurality of electrode portions defining an analytical gap for allowing ions to propagate therethrough along approximately the first direction; and,
    at least an electrical controller for electrically coupling to at least one of the at least a first electrode, the at least a second electrode and the electrode plate for establishing an electrical field within the analytical gap resulting from the application of an asymmetric waveform voltage and a direct current voltage between the at least a first electrode, the at least a second electrode and the electrode plate,
    whereby ions having suitable high field mobility properties for a given combination of applied asymmetric waveform voltage and direct current voltage are selectively transmitted through the analytical gap.

20. An apparatus according to claim 19, wherein at least one of the first plurality of electrode portions and the second plurality of electrode portions is a portion of a formed electrode.

21. An apparatus according to claim 19, wherein the electrode plate is a flat electrode plate.

22. An apparatus according to claim 20, wherein the other one of the at least one of the first plurality of electrode portions and the second plurality of electrode portions comprises an electrode stack having a length and comprising a plurality of rods, each rod of the plurality of rods being spaced apart from an adjacent rod in a direction along the length of the electrode stack.

23. A method of separating ions comprising the steps of:
introducing ions into a first space defined between adjacent electrode plates of a stacked parallel plate high field asymmetric waveform ion mobility spectrometer;
performing a first separation of the ions within the first space, to selectively transmit a subset of the ions along a first direction between a first end of the electrode plates and a second end of the electrode plates that is opposite the first end;
performing a second separation of the ions within a second space, the second space being defined between edge surfaces of the second end of each of the electrode plates and at least another electrode, to selectively transmit some of the subset of the ions along a second direction approximately transverse to the first direction and toward an ion outlet.

24. A method according to claim 23, comprising the step of providing a first flow of a gas within the first space along the first direction between the first end of the electrode plates and a second end of the electrode plates and providing a second flow of a gas within the second space along the second direction and toward the ion outlet.

25. A method according to claim 23, comprising the step of providing a flow of a gas within the first space along the first direction between the first end of the electrode plates and a second end of the electrode plates and providing a potential gradient within the second space for directing ions propagating therein along the second direction toward the ion outlet.

* * * * *